United States Patent [19]

Madec et al.

[11] 4,213,763
[45] Jul. 22, 1980

[54] METHOD AND DEVICE FOR ANALYZING GEOLOGICAL SEDIMENTS AND FOR DETERMINING THEIR ORGANIC SULFUR CONTENT

[75] Inventors: Marcel Madec, Suresnes; Jean Espitalie, Le Vesinet; Jean-Loup Laporté, Rulil-Malmaison; Imré Barsony, Clamart, all of France

[73] Assignee: Institut Francais du Petrole, France

[21] Appl. No.: 866,065

[22] Filed: Dec. 30, 1977

[30] Foreign Application Priority Data

Dec. 30, 1976 [FR] France .................................. 76 39539

[51] Int. Cl.² ...................... G01N 31/12; G01N 33/24
[52] U.S. Cl. ............. 23/230 EP; 23/230 PC; 422/80
[58] Field of Search ...... 23/230 PC, 253 PC, 230 EP, 23/254 EF; 422/80, 78

[56] References Cited

U.S. PATENT DOCUMENTS

| | | | |
|---|---|---|---|
| 2,634,360 | 4/1953 | Kusa | 23/253 PC X |
| 2,888,332 | 5/1959 | Aites | 23/253 PC |
| 3,129,062 | 4/1964 | Onekiehong et al. | 23/254 EF X |
| 3,489,523 | 1/1970 | Clardy et al. | 23/254 EF X |
| 3,574,549 | 4/1971 | Eggertsen | 23/230 PC |
| 3,585,003 | 6/1971 | Scolnick | 23/254 EF |
| 3,650,696 | 3/1972 | Eads | 23/230 PC |
| 3,838,969 | 10/1974 | Dugan | 23/253 PC X |
| 3,880,587 | 4/1975 | Szakasits et al. | 23/253 PC X |
| 3,953,171 | 4/1976 | Espitalié et al. | 23/253 PC X |

Primary Examiner—Arnold Turk
Attorney, Agent, or Firm—Craig & Antonelli

[57] ABSTRACT

A sample of the studied sediments is heated in a non-oxidizing atomosphere.

The organic material of the sediment is then pyrolyzed and the released products are oxidized. The sulfur content of the sulfur compounds produced by this oxidation is continuously measured in relation with the temperature in the form of an electric signal. The overall sulfur content of the sample is utilized in combination with a parameter characterizing the sample to determine the degree of evolution of the organic material in the sediment.

13 Claims, 7 Drawing Figures

METHOD AND DEVICE FOR ANALYZING GEOLOGICAL SEDIMENTS AND FOR DETERMINING THEIR ORGANIC SULFUR CONTENT

The present invention relates to a method and a device for analyzing geological sediments and, in particular, for determining their organic sulfur content. It is an object of the invention to obtain the above data very rapidly and on the basis of small samples.

The methods used up to now for determining the sulfur content of rocks are time-consuming, expensive and no precise information on the organic sulfur can be obtained.

A method which is very often used to determine the sulfur organic compounds content of the hydrocarbons is gas photometry. However this technique which can only be used for analyzing very small gas volumes, cannot be employed for direct measurements on a raw rock sample, since the detector of sulfur products is very sensitive to fouling.

Moreover the detector response is linear only within a narrow range of concentrations of sulfur products. Furthermore this type of apparatus has numerous cold spots and consequently, as long as condensation must be avoided, the application of the apparatus is limited to the analysis of gases at moderate temperature, generally below 200° C.

The methods for analyzing sediments wherein a sample is pyrolyzed in an oxidizing atmosphere cannot be applied to geological sediments, since they result in a precocious oxidation of pyrite $FeS_2$, producing sulfur dioxide $SO_2$, which can hardly be distinguished from the oxidation products of the organic material contained in the sample.

Briefly stated, according to the method of the present invention, a sample of sediment to be studied, eventually of small size, is heated to a temperature capable of pyrolyzing the organic material contained therein. This pyrolysis can be carried out in an atmosphere of inert gas, such as nitrogen, helium, argon, etc... or in hydrogen atmosphere. The pyrolysis products are burnt, whereby the organic sulfur compounds are converted into sulfur dioxide ($SO_2$) in admixture with a small proportion of sulfur trioxide ($SO_3$), then a suitable detector determines the sulfur initial content of the pyrolyzed organic material of the sample.

It will be optionally possible to simultaneously determine the amount of hydrocarbon products resulting from the pyrolysis of the insoluble organic material of the sample.

This double determination makes it then possible to characterize the type of organic material contained in the sample and optionally to precisely determine the degree of evolution of this organic material, as described hereinunder more in detail.

The invention will be clearly understood and its advantages made apparent from the description of a non-limitative embodiment illustrated by the accompanying drawings wherein.

Figure 1:
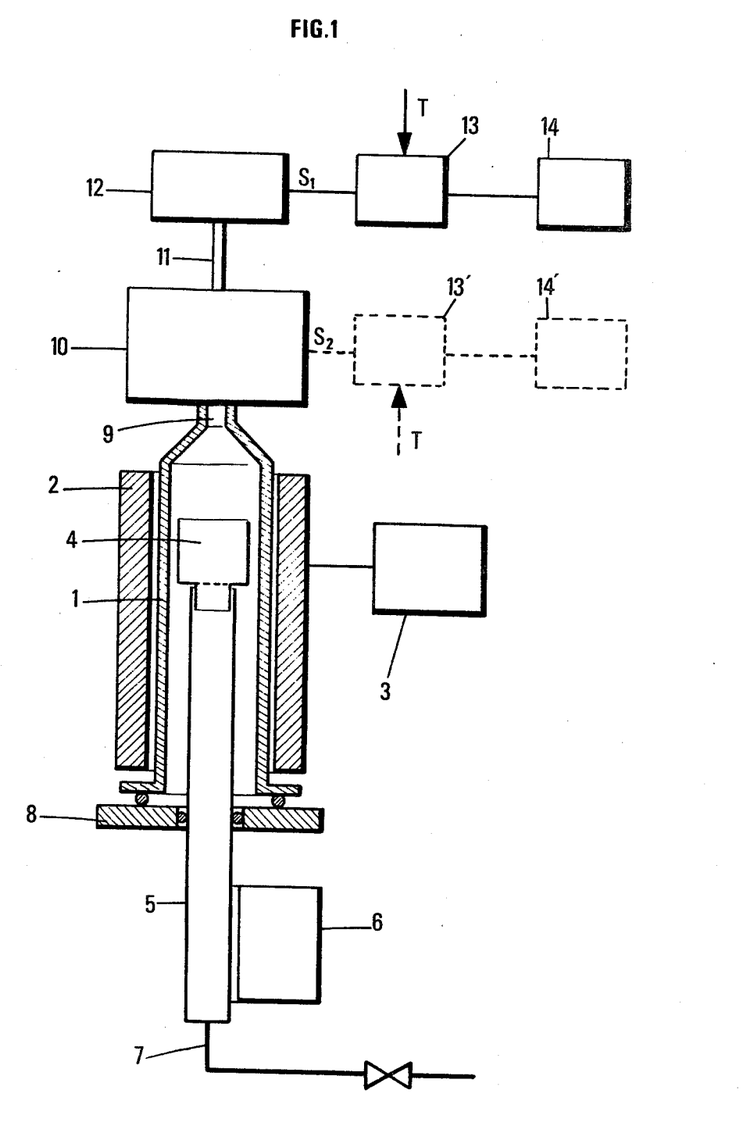
FIG. 1 diagrammatically illustrates an embodiment of the device according to the invention.

A particular embodiment of a device for carrying out the method according to the invention is diagrammatically shown in FIG. 1.

This apparatus comprises a chamber 1 such as a heating chamber or a chamber which can be heated. In the illustrated embodiment, the apparatus comprises a device 2 for heating the whole chamber. This heating device 2 may be of any known type and for example surrounds chamber 1. It is however also possible to constitute chamber 1 of an electrically conducting material fed with electric current to heat the chamber by Joule effect. The heating device 2 is supplied with power from power source (not shown).

The operation of the heating device 2 is monitored by a suitable control element 3, so that the temperature within chamber 1 has a determined value or varies according to a predetermined law. This control element will for example be a heating programmer means of any commercially available type and need not therefore to be described in detail.

The apparatus also comprises a cup 4 receiving the sample to be analyzed. This cup may be displaced, so as to be introduced into chamber 1, by any suitable means, such as, for example, a piston 5 associated to manually or automatically actuated displacement means 6 which may comprise a cylinder forming with piston 5 a double-acting jack, this jack being connected to a source of pressurized fluid or to a toothed wheel (or pinion) which can be rotated and co-operates with a rack integral with piston 5. Piston 5 is preferably hollow and its end opposite the end which carries cup 4 is connected to a pipe 7 supplying a non-oxidizing gas, such as an inert gas (nitrogen, helium . . . etc . . . ), or hydrogen.

An insulating and sealing device 8 is provided at the periphery of piston 5. This device may optionally be displaceable to facilitate the introduction of the sample into cup 4.

Chamber 1 is connected through a pipe 9 to a device 10 for burning the products discharged from chamber 1. This device 10 communicates through a pipe 11 with a detector 12 of sulfur dioxide and of sulfur trioxide, this detector being adapted to deliver a signal $S_1$ representing the sulfur content of the sulfur containing products.

This detector may be of any known type, such as, for example, a high sensitivity infra-red detector, a microcoulometer, an automatically regulated PH-meter, a conductimeter, a UV fluorescence detector, an automatic colorimeter, a flame photometer, or specific solid state detectors, such as electro-chemical sensors, doped transistors, etc . . . .

With some types of detectors, such as for example infra-red detectors it will be necessary to place upflow of detector 12 a trap for retaining water contained in the gas outflow from the flame ionization detector. This trap may comprise solid adsorbents (molecular sieve, calcium chloride, silica-gel, etc . . . ) or contain concentrated sulfuric acid. In the case of a solid adsorbent, a heating device with a system of switch valves permits regeneration of the trap between two analyses.

Signal $S_1$ can be transmitted to a recording device 13 which receives on another input terminal a signal T representing the temperature within chamber 1. Signal $S_1$ may be optionally transmitted to a summing device 14 such as an integrator which may display the overall amount of sulfur measured by detector 12.

The element 10 may be of any known type, comprising for example a combustion chamber equipped with a burner.

This element 10 will preferably be adapted to deliver a signal $S_2$ representing the amount of hydrocarbon products discharged from chamber 1. In this case the element 10 may be a flame ionization detector of conventional use in gas chromatography analyses. This detector will however preferably be designed as shown in FIG. 2.

Signal $S_2$ is transmitted to an input terminal of a recording device 13' shown in dotted line in FIG. 1, this device receiving on another input terminal a signal T representing the temperature within the chamber. Signal $S_2$ is also transmitted to a summing unit 14', also shown in dotted line, capable of indicating the overall amount of hydrocarbon products discharged from chamber 1.

In FIG. 1 the recording device 13' and summing device 14' are shown separate from the recording device 13 and the summing unit 14, but it would be possible, without departing from the scope of the present invention, to use only one recording device and one summing unit having a plurality of input terminals and capable of simultaneously processing a plurality of signals.

Figures 2, 2A:
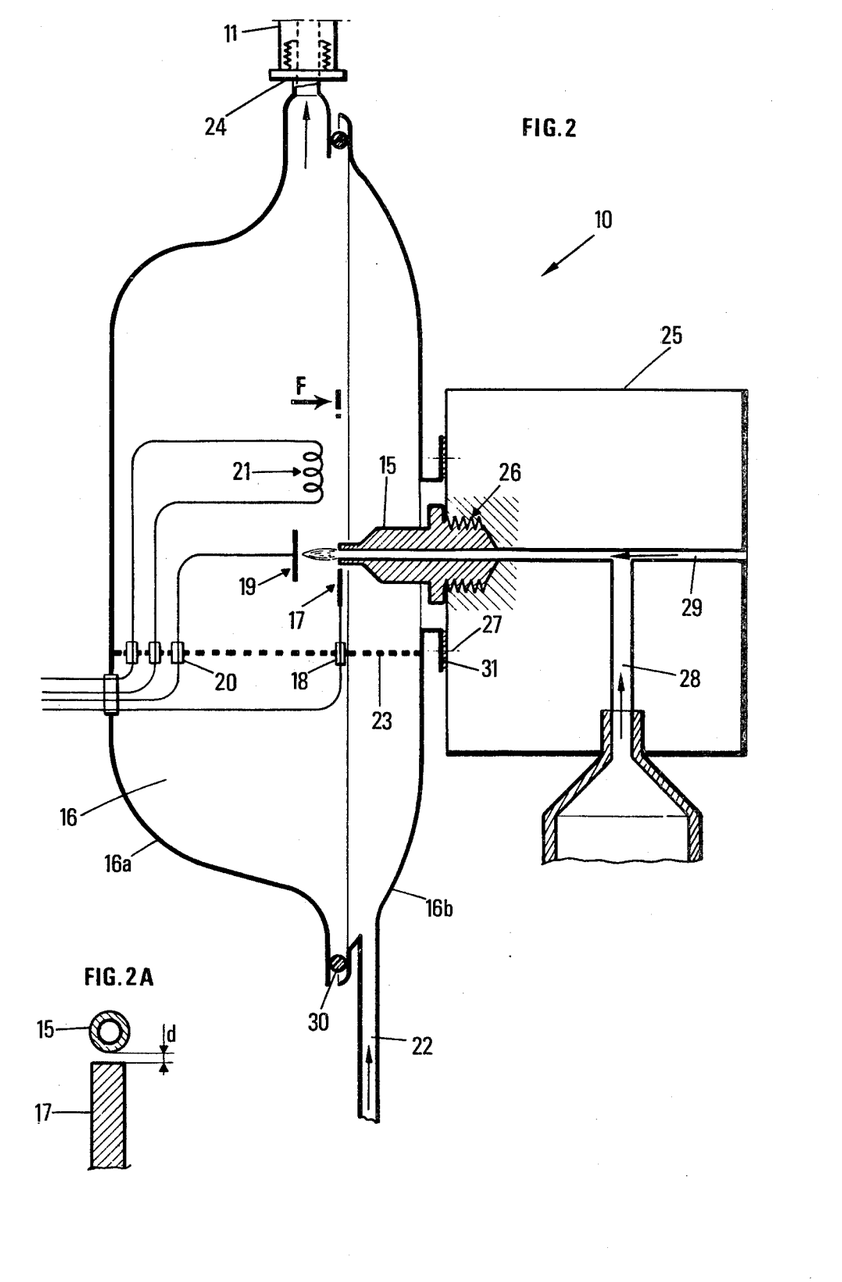
FIGS. 2 and 2A are detail views of element 10.

FIG. 2 illustrates a particular embodiment of element 10 capable of delivering signal $S_2$. This element is a flame ionization detector. It comprises a burner 15 opening in a combustion chamber 16 housing a polarization electrode 17 held in position, as described hereinunder, by insulating support member 18, a collector electrode 19 held in position by an insulating support member 20, and means 21 for lighting the flame, such as an electric filament. In the lower part of chamber 16, a pipe 22 supplies a combustion sustaining gas, such as air, a grid 23 located between the air inlet and the burner providing a good distribution of the air. Combustion chamber 16 communicates at its upper part with pipe 11 to which chamber 16 is connected through a connecting member 24.

The head of burner 15 and the combustion chamber 16 are secured to a supporting block 25, through threading 26 and securing bolts 27 respectively. This supporting block 25 is secured to chamber 1 and maintained at a determined temperature, substantially equal to the maximum temperature reached by chamber 1, through any suitable means using for example heat insulating means (not illustrated). Block 25 comprises a duct 28 interconnecting chamber 1 and burner 15, and duct 29 simultaneously connecting burner 15 to a source of gaseous fuel, such as hydrogen (not illustrated).

Element 10, designed in accordance with the invention, differs from conventional flame ionization detectors in that burner 15 is made of a single conducting metal piece which is at earth potential, whereas the polarization electrode 17, consisting of a thin blade of conducting material is located near that end of burner 15 where the flame is generated, at a distance "d" from this end of about 0.1 to 0.2 mm, as diagrammatically shown by FIG. 2A, which is a view of the burner end along arrow F of FIG. 2. Moreover, the combustion chamber 1, whose constituting parts 16a and 16b are electrically connected to the earth, is sealed by using suitable gaskets, such as gasket 30 made of Teflon, positioned between the two parts 16a and 16b, or the metal gasket 31 whereby is achieved the sealing between combustion chamber 16 and support 25. Thus the combustion within chamber 16 can be accurately controlled and the combustion products transmitted to detector 12 in their entirety.

The apparatus operates as follows:

A sample of studied geological sediment is placed into cup 4. This sample will generally be of a small size and weigh a few milligrams.

This sample will be optionally subjected to preliminary treatments, such as drying, grinding, extraction by other processes of the hydrocarbons contained in the sample . . . etc . . . . As a rule this sample may be subjected to any treatment which does not raise its temperature above 250° C. Hereinafter there is contemplated, by way of example, a measurement performed on a sample of drill cuttings collected during a drilling operation, this sample being not subjected to any preliminary treatment.

Cup 4 (FIG. 1), containing the sample, is introduced into chamber 1 by displacing piston 5. A non-oxidizing gas is introduced into chamber 1 through pipe 7. This carrier gas scavenges chamber 1 and drives towards the measuring instruments the gaseous products of any, released by the sample.

Control element 3 then energizes the heating device 2 so that temperature within chamber 1 progressively increases, up to a maximum value, at most equal to 600° C. and generally from 500° C. to 550° C., at which a possible decomposition of pyrite $FeS_2$ does not interfere with the results. This temperature variation is performed at a rate of from 1° C./minute to 50° C./minute, preferably from 5° C. to 25° C./minute.

Figure 3:
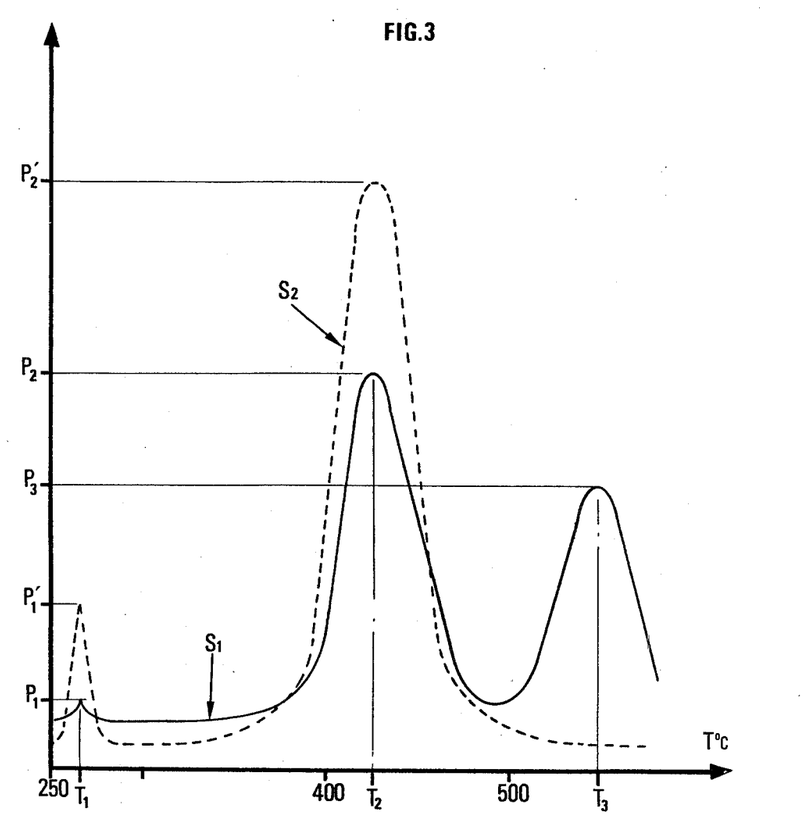
FIG. 3 shows signals $S_1$ and $S_2$ delivered by the device.

The temperature increase within chamber 1, first results, up to 350° C., in a vaporization of the hydrocarbons contained in the sample. These hydrocarbons, driven by the carrier gas, are burnt in the combustion chamber of element 10. The combustion gases, which mainly contain sulfur dioxide ($SO_2$) with a very small amount of sulfur trioxide ($SO_3$) resulting from the combustion of sulfur products contained in the hydrocarbons, are transmitted to detector 12. The latter measures continuously the sulfur contents of the combustion gases and delivers a signal $S_1$ recorded at 13 in dependence with temperature T within chamber 1. The signal $S_1$, in solid line in FIG. 3, shows, at temperature $T_1$, a first peak of amplitude $P_1$. When the temperature within the chamber 1 increases above 350° C., the organic material of the sample is pyrolyzed. The resulting pyrolysis products are burnt in element 10 and the sulfur compounds of the organic material mainly consist of sulfur dioxide with a very small amount of sulfur trioxide ($SO_3$). The combustion products are transferred to detector 12 and the signal $S_1$ delivered by this detector shows, at temperature $T_2$, a peak of amplitude $P_2$. Peak $P_2$ represents the organic sulfur content of the sample. Signal $S_1$ may show a peak of amplitude $P_3$ at a temperature $T_3$ higher than $T_2$. This peak, when it occurs corresponds to the amount of sulfur resulting from the decomposition of iron pyrite $FeS_2$.

In the case where an element 10 of the type shown in FIG. 2 is used, the device may simultaneously and continuously deliver a signal $S_2$ which represents the amount of hydrocarbon products discharged from chamber 1. Signal $S_2$ is shown in dotted line in FIG. 3.

This signal $S_2$, recorded versus temperature T by recorder 13', has a first peak of amplitude $P'_1$ corresponding to the hydrocarbons contained in the sample, and a peak of amplitude $P'_2$ corresponding to the hydrocarbon products resulting from the pyrolysis of the insoluble organic material of the sample.

Signals $S_1$ and $S_2$ may optionally be transmitted to the summing devices 14, 14' which deliver signals representing respectively the overall amounts of sulfur and of hydrocarbon products resulting from the treatment which the sample has been subjected to.

Such data may of course be supplied in the form of either absolute values or relative values, i.e. as contents or concentrations.

The authors have discovered that the organic sulfur content of a sediment characterizes the degree of evolution of the organic material in this sample.

Figure 4:
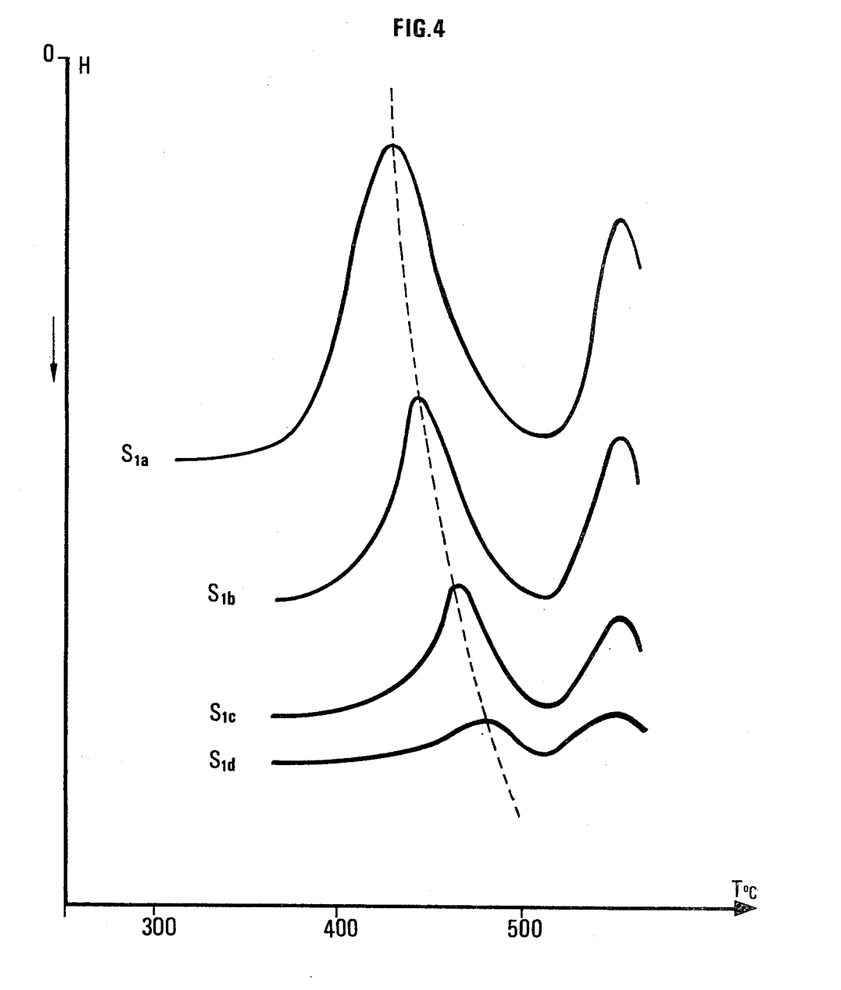
FIG. 4 shows signals $S_1$ resulting from the analysis of samples collected at different depths and belonging to a single sedimentary series.
Figure 5:
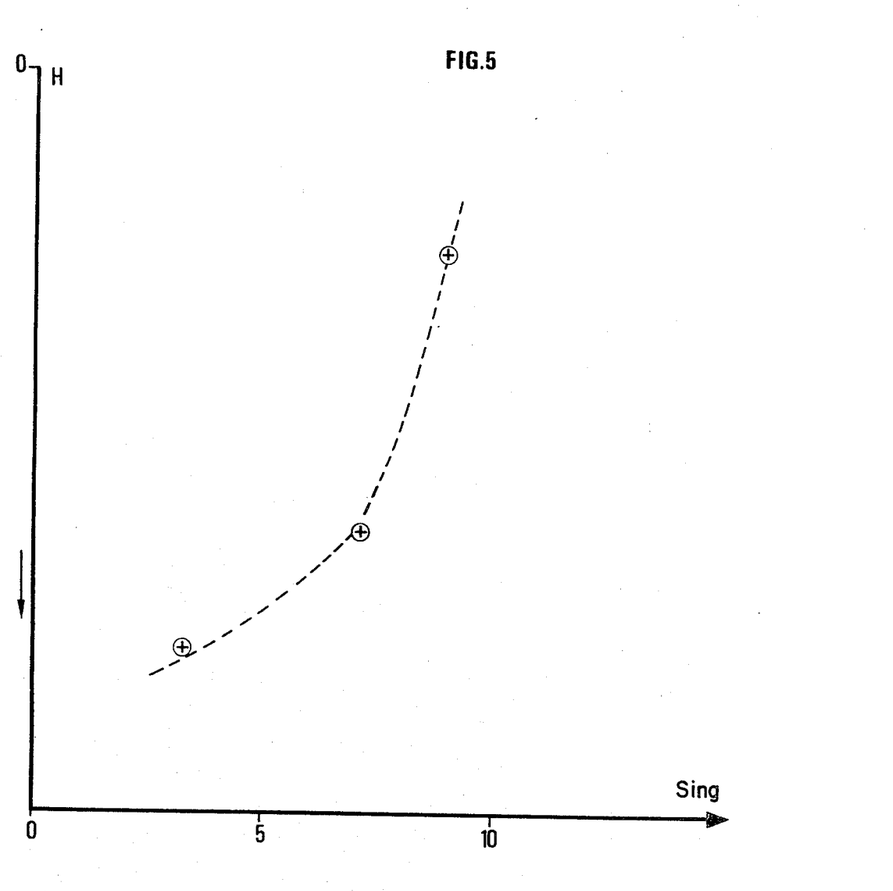
FIG. 5 shows the degree of evolution of the organic material of a sedimentary series.

Thus in a homogeneous sedimentary series, for example lower Toarcian of the Paris basin, a decrease in the organic sulfur content corresponds to an increasing burying depth H of the sediment. An example of this phenomenon is given by FIG. 4 which represents the signals $S_{1a}$, $S_{1b}$, $S_{1c}$ and $S_{1d}$ produced by four sediment samples a, b, c and d of the same weight, collected at respective depths of 800 m, 1,500 m, 2,000 m and 3,000 m. It also appears that the temperature of maximum release of sulfur products, during the pyrolysis of the organic material, increases with the burying depth, thus with the degree of evolution of the organic material. The degree of evolution of an organic material of a known type in an homogeneous sedimentary series can also be evaluated by plotting the curve of FIG. 5, representing the value of signal $S_1$ i.e. the organic sulfur content of the sediments, versus their burying depths. Similarly it is possible to plot the curve representing the amount of organic sulfur versus the temperature $T_2$ of peak $P_2$ in the signal $S_1$ of each sample.

Moreover it has been ascertained that, by determining the hydrocarbon products resulting from the pyrolysis of the insoluble organic material (Peak $P_2$, FIG. 3) and the sulfur organic compounds in the products resulting from the pyrolysis of a sediment, it is possible to ascertain two characteristic parameters, when the amount of organic carbon in the sample is known:

the hydrogen index $I_H$, expressed in mg of hydrocarbon products per gram of organic carbon, and
the sulfur index $I_S$, expressed in mg of sulfur per gram of organic carbon.

Figure 6:
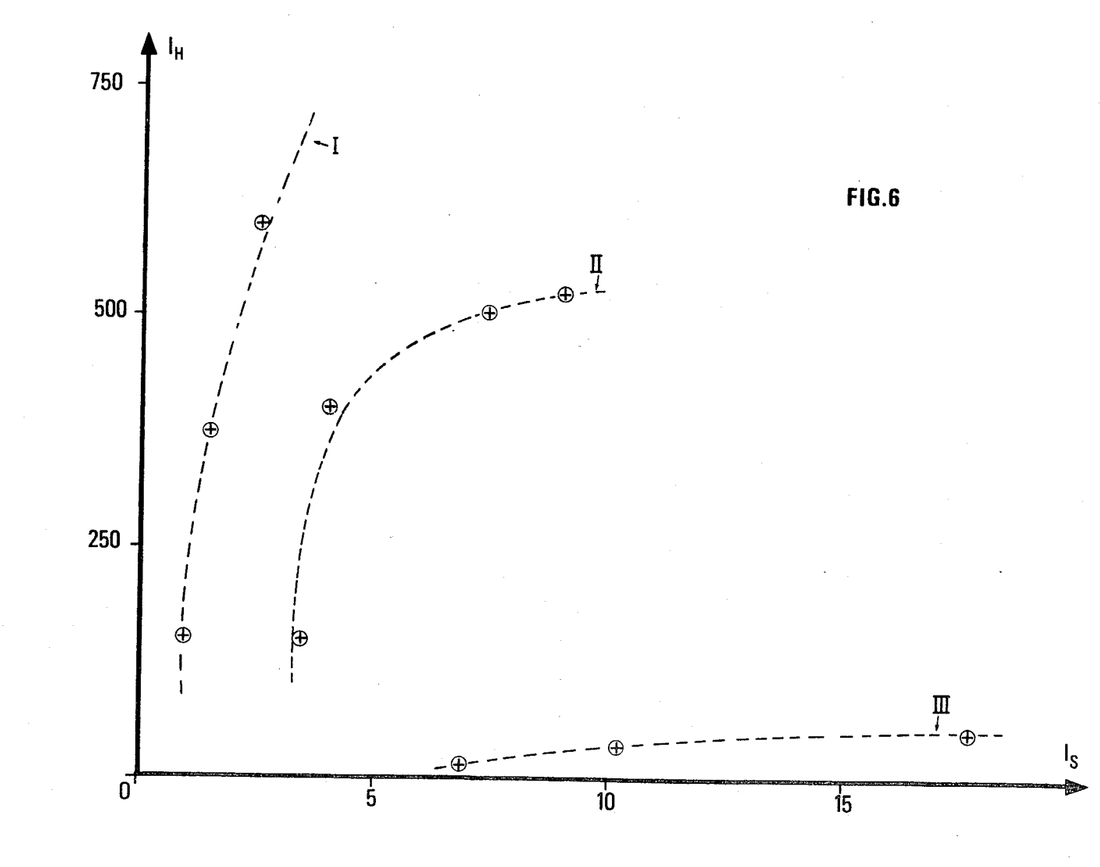
FIG. 6 represents, for organic materials of different origins, the curves of the hydrogen index versus the sulfur index.

It can be ascertained that, for organic materials of different origins, the curves $I_H = f(I_S)$ are clearly distinct. As shown by FIG. 6:

organic material of algar origin (curve No. I) are characterized by a high hydrogen index and a relatively low sulfur index $I_S$ and the sulfur index decreases rather slowly with an increasing burying depth, organic material of detrital origin (curve No. III) have, on the contrary, a low hydrogen index $I_H$ and a high sulfur index $I_S$, and their sulfur index decreases rapidly with an increasing burying depth, organic material of marine origin (curve No. II) have a hydrogen index $I_H$ and a sulfur index $I_S$ comprised between curves I and III. The sulfur index $I_S$ decreases rather rapidly during the first part of the evolution, then when a certain level is reached, the sulfur index $I_S$ is stabilized, while the hydrogen index decreases more rapidly.

The invention also permits correlations between mother or source rocks and oil.

It appears in fact that:

curves of the type of curve No. I are relative to mother rocks which produce oils of relatively low sulfur content (at most 1%), curves of the curve No. II correspond to mother rocks producing oils of higher sulfur contents (up to 3.5 or 4%) and curves of the type of curve No. III correspond to bad mother rocks, for which it was not possible to make comparisons with the sulfur content of the corresponding oil.

In the field of coals, knowledge of the content of organic sulfur compounds in the pyrolysis volatile products permits the determination of the degree of evolution. As it is well known in effect the more evolved is a coal the lower its sulphur content. Thus lignite, has a relatively high sulfur content, while anthracite contains practically no sulfur.

What we claim is:

1. A method for determining the degree of evolution of organic material in a plurality of samples of a sedimentary series, comprising, for each sample:

placing the sample in a non-oxidizing atmosphere,
    heating the sample to a determined temperature at which the organic material of the sample is pyrolyzed, forming pyrolysis products,
    oxidizing or burning the resulting pyrolysis products, forming oxidation products,
    detecting the sulfur compounds contained in the oxidation products,
    generating a signal representing the overall sulfur content of the oxidation products, for each sample, and
    determining from the value of said signal, in combination with a parameter characterizing the sample, the degree of evolution of the organic material in the sample.

2. A method according to claim 1, wherein the signal representing the overall sulfur content of the oxidation products, for each sample, is generated, after detecting the sulfur compounds contained in the oxidation products, by continuously measuring as a function of the heating temperature of the sample the sulfur content of said sulfur compounds, producing an output signal representing this sulfur content versus the heating temperature of the sample and transmitting the output signal to a summing device which generates the signal representing the overall sulfur content of the oxidation products, for each sample.

3. A method according to claim 1, wherein said parameter characterizing the sample is the depth at which the sample has been collected.

4. A method according to claim 1, wherein said parameter characterizing the sample is the temperature at which the pyrolysis of organic material of the sample releases the greatest amount of volatile products.

5. A method according to claim 1, comprising determining for each sample the value of the temperature for which the amount of organic sulfur contained in the oxidation products of the sample is maximum, and deriving from the so-determined temperatures the degree of evolution of the organic material in the different samples.

6. A method for determining the nature of the organic material contained in a plurality of samples of a sedimentary series when knowing the amount of organic carbon in each sample, comprising the following steps carried out on each sample:

placing the sample in a non-oxidizing atmosphere, heating the sample to a determined temperature at which the organic material of the sample is pyrolyzed, forming pyrolysis products, oxidizing or burning the resulting pyrolysis products, forming oxidation products, detecting the sulfur compounds contained in the oxidation products, generating a first signal representing the overall sulfur content of the oxidation products, generating a second signal representing the overall amount of hydrocarbon products resulting from the sample pyrolysis up to a temperature from 500° C. to 550° C., determining the value of the ratio of the overall amount of hydrocarbon products to the overall amount of organic carbon, determining the value of the ratio of the overall amount of sulfur to the overall amount of organic carbon, and deriving from these two values the nature of the organic material contained in the sample.

7. A method according to claim 6, wherein the first signal representing the overall sulfur content of the oxidation products is generated, after detecting the sulfur compounds contained in the oxidation products, by continuously measuring as a function of the heating temperature of the sample the sulfur content of said sulfur compounds, producing an output signal representing this sulfur content versus the heating temperature of the sample and transmitting the output signal to a summing device which generates the first signal representing the overall sulfur content of the oxidation products.

8. A method for determining the degree of evolution of the organic material in a sample of a geological sediment, comprising:

placing the sample in a non-oxidizing atmosphere, heating the sample to a determined temperature at which the organic material of the sample is pyrolyzed, forming pyrolysis products, oxidizing or burning the resulting pyrolysis products, forming oxidation products, detecting the sulfur compounds contained in the oxidation products, generating a signal representing the overall sulfur content of the oxidation products of said sample, and determining from the values of said signal, in combination with a parameter characterizing the sample, the degree of evolution of the organic material in the sample.

9. A method according to claim 8, wherein the signal representing the overall sulfur content of the oxidation products of said sample is generated, after detecting the sulfur compounds contained in the oxidation products, by continuously measuring as a function of the heating temperature of the sample the sulfur content of said sulfur compounds, producing an output signal representing this sulfur content versus the heating temperature of the sample, and transmitting the output signal to a summing device which generates the signal representing the overall sulfur content of the oxidation products of said sample.

10. A method for determining the nature of the organic material contained in a sample of a geological sediment, when knowing the amount of organic carbon in the sample, wherein the following steps are carried out:

placing the sample in a non-oxidizing atmosphere, heating the sample to a determined temperature at which the organic material of the sample is pyrolyzed, forming pyrolysis products, oxidizing or burning the resulting pyrolysis products, forming oxidation products, detecting the sulfur compounds contained in the oxidation products, generating a first signal representing the overall sulfur content of the oxidation products, generating a second signal representing the overall amount of hydrocarbon products, resulting from the sample pyrolysis up to a temperature from 500° C. to 550° C., determining the value of the ratio of the overall amount of hydrocarbon products to the overall amount of organic carbon, determining the value of the ratio of the overall amount of sulfur to the overall amount of organic carbon, and deriving from these two values the nature of the organic material contained in the sample.

11. A method according to claim 10, wherein the first signal representing the overall sulfur content of the oxidation products is generated, after detecting the sulfur compounds contained in the oxidation products, by continuously measuring as a function of the heating temperature of the sample the sulfur content of said sulfur compounds, producing an output signal representing this sulfur content versus the heating temperature of the sample, and transmitting the output signal to a summing device which generates the first signal representing the overall sulfur content of the oxidation products.

12. A device for analyzing geological sediments on the basis of a small sample comprising in combination a chamber provided with heating means and means for controlling the heating means so as to produce in the chamber a temperature capable of pyrolyzing the organic material contained in the sample, said chamber also having an orifice for removing the pyrolysis products from the chamber, a displaceable sample holder, means for positioning the sample holder in the chamber, means for supplying a pressurized non-oxidizing gas to take away through said orifice of the chamber the pyrolysis products, a flame ionization detector connected to the chamber through the orifice and comprising combustion means for burning the pyrolysis products and measuring means for producing as a function of the temperature in the chamber a signal $S_2$ representing the amount of hydrocarbon products resulting from the pyrolysis of the insoluble organic material of the sample, detection means connected to the flame ionization detector adapted to generate a signal $S_1$ representing the sulfur content of the combustion products as a function of the temperature in the chamber, wherein the flame ionization detector comprises a burner having two ends, the first end being connected to a source of gaseous fuel and to the chamber, a combustion space housing the second end of the burner, two electrodes in the combustion space respectively adapted to be connected to suitable electric voltage sources to produce an electric field, a first of the electrodes constituting a collector electrode and the second electrode being positioned in the vicinity of the second end of the burner, said burner being made of an electrically conductive material and connected to ground, and wherein said combustion space is sealed and comprises, at its lower part, a gaseous fuel inlet and at its upper part an outlet port for the combustion products, this outlet port communicating with the detection means.

13. A device as in claim 12, wherein said second electrode is positioned 0.1 to 0.2 mm from the second end of the burner.

* * * * *